US008445536B2

(12) United States Patent
Ohta et al.

(10) Patent No.: US 8,445,536 B2
(45) Date of Patent: May 21, 2013

(54) ARGININE-CONTAINING COMPOSITIONS AND METHODS FOR INCREASING BLOOD FLOW USING SAME

(75) Inventors: Fumio Ohta, Kawasaki (JP); Tomo Takagi, Kawasaki (JP); Hiroyuki Sato, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 658 days.

(21) Appl. No.: 11/278,029

(22) Filed: Mar. 30, 2006

(65) Prior Publication Data
US 2006/0228396 A1    Oct. 12, 2006

(30) Foreign Application Priority Data

Mar. 31, 2005 (JP) ................. 2005-103590

(51) Int. Cl.
A61K 31/195 (2006.01)
A61K 31/16 (2006.01)

(52) U.S. Cl.
USPC ............ 514/565; 514/561; 514/626; 514/929

(58) Field of Classification Search
None
See application file for complete search history.

(56) References Cited

U.S. PATENT DOCUMENTS

| | | | | |
|---|---|---|---|---|
| 5,134,125 A * | 7/1992 | Hara et al. | ........................ | 514/19 |
| 5,658,895 A * | 8/1997 | Aoi et al. | ........................ | 514/58 |
| 5,895,658 A | 4/1999 | Fossel | | |
| 5,902,829 A * | 5/1999 | Schneider et al. | | |
| 5,922,332 A | 7/1999 | Fossel | | |
| 6,001,878 A * | 12/1999 | Van Leeuwen et al. | ...... | 514/563 |
| 6,060,466 A * | 5/2000 | Whittemore et al. | ......... | 514/183 |
| 6,207,713 B1 | 3/2001 | Fossel | | |
| 6,274,564 B1 * | 8/2001 | Sarill et al. | ........................ | 514/52 |
| 6,291,525 B1 * | 9/2001 | Nissen | ........................ | 514/557 |
| 6,346,264 B1 * | 2/2002 | White | ........................ | 424/439 |
| 6,818,669 B2 | 11/2004 | Moskowitz et al. | | |
| 6,864,230 B2 * | 3/2005 | Ostrom | ........................ | 514/2 |
| 7,914,814 B2 | 3/2011 | Fossel | | |
| 2002/0182162 A1 | 12/2002 | Shahinpoor et al. | | |
| 2003/0018076 A1 | 1/2003 | Fossel | | |
| 2003/0032616 A1 | 2/2003 | Moskowitz et al. | | |
| 2004/0092592 A1 | 5/2004 | Kaplan | | |
| 2004/0192553 A1 | 9/2004 | Kurauchi et al. | | |
| 2006/0229256 A1 * | 10/2006 | Anthony et al. | ................. | 514/19 |

FOREIGN PATENT DOCUMENTS

| | | |
|---|---|---|
| JP | 08198748 | 8/1996 |
| JP | 09241156 | 9/1997 |
| JP | 2001187736 | 7/2001 |
| JP | 2002-515401 | 5/2002 |
| JP | 2002-539257 | 11/2002 |
| JP | 2004-262878 | 9/2004 |
| WO | WO95/18608 | 7/1995 |
| WO | WO 02062329 A1 * | 8/2002 |

OTHER PUBLICATIONS

"L-arginine infusion promotes nitric oxide-dependent vasodilation, increases regional cerebral blood flow, and reduces infarction volumne in the rat", Morikawa et al., Stoke, vol. 25, pp. 429-435, 1994.*
"Glutamine-enriched enteral diet increases splanchnic blood flow in the rat", Houdijk et all, AJP Gastrointest Liver Physiol 267:G1035-G1049, 1994.*
Fossel, E.T. (Diabetes Care, vol. 27, No. 1, Jan. 2004, pp. 272-290).*
Rosick, E. R., "Arginine Fights Coronary Artery disease", www.life-enhancment.com, 2002.*
Schellong et al., Clin Sci, 1997, abstract, 93(2);159-65.*
Bolotin et all, Asian Cardiovasc Thorac Ann 2007;15:463-7.*
Marcora et al., Clinical Nutrition, vol. 24, pp. 442-454, available online Apr. 21, 2005.*
Matheson et al., The American Journal of Surgery, 2008, vol. 196, pp. 293-299.*
Bode-Böger, S. M., et al., "L-arginine-induced vasodilation in healthy humans: pharmcokinetic-pharmacodynamic relationship," J. Clin. Pharmacol. 1998;46:489-497.
Hotta, H., et al., Biomedical Gerontology 2001;25(2):83-88.
McPherson, R. W., et al., "Cerebral Blood Flow in Primates Is Increased by Isoflurane over Time and Is Decreased by Nitric Oxide Synthase Inhibition," Anesthesiology 1994;80:1320-1327.
Nakaki, T., et al., "The Arginine Paradox," Folia Pharmacol. Jpn. 2002;119:7-14.
Yarnitsky, D., et al., "Blood-brain barrier opened by stimulation of the parasympathetic sphenopalatine ganglion: a new method for macromolecule delivery to the brain," J. Neurosurg. 2004; 101:303-309.
Clark, R. H., et al., "Nutritional Treatment for Acquired Immunodeficiency Virus-Associated Wasting Using β-Hydroxy β-Methylbutyrate, Glutamine, and Arginine: A Randomized, Double-Blind, Placebo-Controlled Study," J. Parenteral and Enteral Nutr. 2000;24(3):133-139.
Gupta, V., et al., "Anti-stress and Adaptogenic Activity of L-Arginine Supplementation," eCAM 2005;2(1):93-97.
Litchford, M., et al., "Use of Arginine and Glutamine Supplements to Enhance Wound Healing in a Long-Term Care (LTC) Resident," J. Am. Dietetic Assoc. 2001;101(9):A-49.
Roth, E., "L-arginine-nitric oxide metabolism. Glutamine: a new player in this metabolic game?" Clin. Nutr. 1998;17:1-2.
Dumont, Y., et al., "Supplementation with a low dose of L-arginine reduces blood pressure and endothelin-1 production in hypertensive uraemic rats," Nephrol. Dial. Transplant 2001;16:746-754.
Office Action for Japanese Patent App. No. 2006-098388 (Dec. 12, 2011) with English translation thereof.

* cited by examiner

Primary Examiner — Savitha Rao
Assistant Examiner — Gregg Polansky
(74) Attorney, Agent, or Firm — Shelly Guest Cermak; Cermak Nakajima LLP

(57) ABSTRACT

A composition for increasing blood flow is provided, wherein side effects such as lowering of blood pressure are reduced and blood flow is effectively increased in the capillaries. A composition containing arginine in an amount from 25 mg/kg body weight to 150 mg/kg body weight is also provided. A food composition or a feeding stuff containing the composition is also provided. Method of using the above compositions to increase blood flow is also provided.

3 Claims, No Drawings

ARGININE-CONTAINING COMPOSITIONS AND METHODS FOR INCREASING BLOOD FLOW USING SAME

This application claims priority under 35 U.S.C. §19(a) to JP2005-103590, the entirety of which is hereby incorporated by reference.

BACKGROUND OF THE INVENTION

1. Field of the Invention

The present invention relates to arginine-containing compositions and methods for increasing blood flow using the same. Specifically, the present invention relates to arginine-containing compositions which are formulated as pharmaceutical compositions, food and beverages, animal feed, and the like. Specifically, the present invention also relates to methods using the arginine-containing compositions for increasing blood flow in the capillaries of a patient without lowering the systemic blood pressure.

2. Brief Description of the Related Art

Blood enables the transport of oxygen, nutrients, signaling molecules such as hormones, waste products, and immune cells. Namely, substances are taken up by the blood from the lungs, digestive tract, and endocrine organs, and are propelled by the heartbeat, and transported and supplied to the entire body through the capillaries. Furthermore, waste products and the like are picked up by the blood through the capillaries of the entire body and excreted from the organs, such as the lungs and kidneys. Blood also functions to retain heat in the body by circulating blood that is always maintained at a constant temperature. Thus, blood flow in the capillaries is important for maintaining the vital functions, but it can weaken when stresses occur, such as disease, infection, injury, fatigue, aging, and sudden environmental changes. For example, it is possible that weak blood flow to the brain may be related to cerebrovascular dementia and Alzheimer-type dementia, wherein the weak blood flow causes deterioration of the vital functions (U.S. Patent Application Publication No. 2002182162). Accordingly, it is important to actively increase blood flow under such conditions, so that heat retention in the body is increased and substances which actively enhance the vital functions are effectively transported by the increased blood flow.

Agents which have been used to increase blood flow include calcium antagonists, cellular respiratory activators, antispasm drugs, in vivo enzymes, and the like.

Since these agents also contain substances which reduce blood pressure and affect the blood vessels of the entire body, there is a possibility of not only increasing the blood flow in the capillaries, but also affecting the systemic blood pressure. In addition, some of the agents cause pain, such as in vivo enzymes like kallikrein. Therefore, it is strongly desirable to develop a method which is effective to increase blood flow and that is safe and easy to use.

It has been previously reported that arginine induces vasodilation. As its mode of action, it has been reported that vascular endothelial cells which contain nitric monoxide synthetases synthesize nitric monoxide from arginine, which causes vasodilation. Externally administered arginine immediately synthesizes nitric monoxide, and this action also produces vasodilation. However, dietary-derived arginine does not usually have the same effect (Japanese Patent Unexamined Publication No. 2004-262878).

Though the actions of arginine when ingested has been widely reported, it has been conventionally thought that vasodilation caused by arginine results in a lowering of blood pressure as well as an increase in blood flow. For example, it has been reported that, when 30 g or 6 g of arginine was parenterally administered to human beings having an average weight of 78 kg, the 30 g of arginine lowered blood pressure and vascular resistance, while the 6 g of arginine did not cause either effect (British Journal of Clinical Pharmacology 1998; 46: 489-497. In addition, other methods for increasing blood flow using arginine have been reported. However, in every such case, the dosage of arginine is very high, or the arginine must be combined with other compositions which alone can act to increase blood flow, such as polyphenols (Anesthesiology 1994; 80: 1320-1327, U.S. Patent Application Publication No. 2002/0182162, Japanese Patent Unexamined Publication No. 2004-262878). Therefore, increasing blood flow using solely arginine without lowering blood pressure has never been reported.

SUMMARY OF THE INVENTION

It is an object of the present invention to provide a composition which can effectively increase blood flow in the capillaries while reducing side effects such as low blood pressure.

The inventors carefully observed the changes of blood pressure and blood flow in the capillaries when administering arginine, and found that administration of arginine in a certain dosage range increased blood flow in the capillaries of peripheral organs without lowering blood pressure. The present invention has been completed based of this finding.

Namely, it is an object of the present invention to provide a method for increasing blood flow comprising administering 25 mg/kg body weight to 150 mg/kg body weight arginine per dose to a patient in need thereof.

It is a further object of the present invention to further provide the method as described above, wherein 50 mg/kg body weight to 150 mg/kg body weight arginine per dose is administered.

It is a further object of the present invention to provide the method as described above, wherein the arginine is selected from the group consisting of L-arginine, L-arginine chlorides, and L-arginine derivatives which are metabolized to L-arginine in vivo.

It is a further object of the present invention to provide the method as described above, wherein an amino acid selected from the group consisting of glutamine, pyrrolidone carboxylic acid, glutamic acid, salts or derivatives thereof, and combinations thereof are administered.

It is a further object of the present invention to provide the method as described above, wherein the ratio of arginine to the amino acid is from 1:4 to 4:1 by weight.

It is a further object of the present invention to provide the method as described above, wherein the amino acid is glutamine.

It is a further object of the present invention to provide the method as described above, wherein the glutamine is administered in an amount from 25 mg/kg body weight to 600 mg/kg body weight per dose.

It is a further object of the present invention to provide the method as described above, wherein the glutamine is administered in an amount from 25 mg/kg body weight to 30 mg/kg body weight per dose.

It is a further object of the present invention to provide a method for preventing, diminishing, or treating a condition selected from the group consisting of dementia, sensitivity to cold, stiff shoulders, dullness, and muscular fatigue comprising administering 25 mg/kg body weight to 150 mg/kg body weight arginine per dose to a patient in need thereof.

It is a further object of the present invention to provide a composition comprising 25 mg/kg body weight to 150 mg/kg body weight arginine.

It is a further object of the present invention to provide a pharmaceutical composition for preventing, diminishing, or treating a condition selected from the group consisting of dementia, sensitivity to cold, stiff shoulders, dullness, and muscular fatigue comprising the composition as described above.

It is a further object of the present invention to provide a food composition comprising 25 mg/kg body weight to 150 mg/kg body weight arginine per dose.

It is a further object of the present invention to provide feed comprising the composition as described above.

According to the present invention, blood flow in the capillaries can be effectively increased while inhibiting side effects such as low systemic blood pressure.

DETAILED DESCRIPTION OF EXEMPLARY EMBODIMENTS

The arginine which can be used in the present invention includes L-arginine and halides thereof, and preferably chlorides thereof, L-arginine derivatives which are promptly metabolized to L-arginine in vivo such as the derivative forms of acid anhydrides, esters, amides, peptides, and proteins, and peptides containing L-arginine as a constituent amino acid. L-arginine is preferable.

The amount of arginine in the compositions of the present invention is from 25 mg/kg body weight to 150 mg/kg body weight, and preferably 50 to 150 mg/kg body weight. Such amount is considered one dose in the methods of the present invention.

The amount of arginine in the compositions of the present invention is preferably a dosage which increases the concentration of free arginine in the blood plasma by 15 mg to 180 mg, preferably 25 mg to 180 mg, more preferably 50 mg to 180 mg, and yet more preferably 50 mg to 150 mg per 1 mL of blood plasma. The administered dose of the present invention is consistent with these increases. The concentration of the free arginine in the blood plasma can be determined by taking the blood plasma 10 minutes after administering arginine, and using an amino acid analyzer (L8500, the amino acid analyzer produced by Hitachi, Ltd.).

By using the dosages set forth above, blood flow can be effectively increased in the capillaries while inhibiting typical side effects of arginine, such as the lowering of the systemic blood pressure.

In the present invention, when the blood flow increases 20% or more relative to the blood flow before administering the composition of the present invention, it is regarded that the blood flow is increased. When the blood pressure varies by ±11 mmHg relative to the blood pressure before administration of the composition of the present invention, it is regarded as no variation. This is because the control can sometimes vary as much as 19%, and therefore and the blood pressure can indicate less than 12 mmHg.

It is preferable that the compositions of the present invention further contain an amino acid(s), such as glutamine, a pyrrolidone carboxylic acid, glutamic acid, and salts or derivatives thereof. Glutamine is particularly preferable.

The glutamine which can be used in the present invention includes L-glutamine, L-glutamine derivatives which are promptly metabolized to L-glutamine in vivo such as N-acetyl-L-glutamine, and peptides containing L-glutamine as a constituent amino acid. L-glutamine is preferable.

The pyrrolidone carboxylic acid which can be used in the present invention is preferably in L-form. Such acids may form salts with alkali metals such as sodium and potassium, and alkaline earth metals such as calcium, basic amino acids such as arginine and lysine, or amines such as triethanolamine. Furthermore, the acids may form derivatives with alcohols and may be in the form of acid anhydrides, peptides, and proteins, which are constituted from said acid. Sodium salt is preferable.

The glutamic acid which can be used in the present invention includes L-glutamic acid and peptides containing L-glutamic acid as the constituent amino acid. Such acids may form salts with alkali metals such as sodium and potassium, and alkaline earth metals such as calcium, basic amino acids such as arginine and lysine, or amines such as triethanolamine. Furthermore, said acids may form derivatives with alcohols, and also may be in the form of acid anhydrides, peptides, and proteins constituted from said acid. L-glutamine is preferable.

The dosage of the amino acids of the present invention is not particularly limited. However, they are preferably administered in an amount from 6.25 mg/kg body weight to 600 mg/kg body weight per a dose, and more preferably 25 to 300 mg/kg body weight per a dose. The ratio of arginine to the amino acid(s) in the compositions of the present invention is preferably from 1:4 to 4:1 and more preferably from 1:2 to 2:1, by weight. It is preferable that the compositions of the present invention contain arginine and the amino acid(s) in the above-stated ratio range, because the volume of blood flow significantly increases.

The compositions of the present invention have the effect of increasing blood flow, and can be preferably used for preventing, diminishing, or treating cerebrovascular dementia, Alzheimer-type dementia, stiff shoulders, sensitivity to cold, dullness, or muscular fatigue. They are excellently effective in increasing blood flow in peripheral organs, particularly in the skin, muscles, bowel, heart, and brain. The compositions of the present invention can effectively increase blood flow especially in the capillaries of these organs, while inhibiting the lowering of the systemic blood pressure, and, therefore, more effectively distribute blood flow in the body.

In addition to pharmaceutical compositions, other types of compositions of the present invention include foods, health foods, nutritional foods (including supplements), nutritional compositions, or feed for livestock or domestic animals. These food compositions should indicate on their packaging that they are useful for increasing blood flow. The dosage usually varies depending on body weight, health conditions, and the like of the patient ingesting the food composition. When administering to adults, 4.5 g to 27 g, and more preferably 9 g to 27 g of arginine per day is a preferable dose.

For pharmaceutical compositions, the composition can be combined with pharmaceutically acceptable carriers or diluents, e.g., cellulose derivatives such as carboxymethylcellulose and ethylcellulose, starches such as potato starch and corn starch, sugars such as lactose and sucrose, vegetable oils such as peanut oil, corn oil and sesame oil, polyethylene glycol, alginic acid, gelatin, and tarc, oral agents such as tablets, dispersants, pills, granules, capsules, and syrups, injectable agents such as subcutaneously injectable agents, intravenously injectable agents, intramuscular injectable agents, peridural space injectable agents, and intrathecally injectable agents, external agents such as intranasal preparation, transdermal preparation, and ointments suppositories such as rectal suppositories and vaginal suppositories, and intravenous fluids.

The pharmaceutical compositions of the present invention can further contain other active substances typically used in pharmaceutical products such as agents for the central or peripheral nervous system, agents for circulatory organs, hormonal agents, antihormonal agents, vitamin preparation, revitalizers, detoxicating agents, antitumor agents, agents against allergies, galenicals, Chinese herbs, chemotherapeutic agents, biologicals, and diagnostic agents.

The pharmaceutical compositions of the present invention can be orally or parenterally administered via, for example, the bowels or veins.

As for food compositions, nonconventional food forms such as supplements and like are included, as well as conventional food compositions. Furthermore, the food composintions of the present invnetion can be prepared by using the proper additive(s) in accordance with the ordinary methods. Examples of such additives include those typically used in health foods, such as fruit juice to adjust and enhance the palatability, dextrin, cyclic oligosaccharide, sugars (fructose and glucose syrup, sucrose), acidifiers, flavoring agents, green tea powder, fat and fatty oils, emulsifying agents to improve the texture, collagen, whole milk powder, polysaccharide thickeners, and agar (in case of jelly beverages).

The foods of the present invention can be further prepared as health foods by including amino acids, vitamins, eggshell calcium, calcium pantothenate, other minerals, royal jelly, propolis, honey, dietary fibers, agaricus, chitin, chitosan, capsaicin, polyphenol, carotenoid, fatty acids, mucopolysaccharides, coenzymes, and antioxidants.

The compositions of the present invention may also be prepared as feed for mammals such as swine, bovines, sheep, canines, felines, mice, rats, and simians. For example, it can be prepared as a solid or liquid additive in animal feed in accordance with the known methods of the aforementioned technical field.

The product forms of the compositions of the present invention are not particularly limited, and include product forms which are typically used for delivery of amino acids. For oral administration, examples include powder, granules, tablets, liquid (beverages, jelly beverages), and candies (such as chocolates), wherein a suitable excipient(s) is used, or the mixture of one or two kinds of the above amino acids. For intravenous administration, examples include transfusions and aqueous solutions containing one or two kinds of the above amino acids, and amino acid powders, which can be added before administration.

The blood flow in the capillaries is an important outcome measure in the present invention, Capillary blood flow can be measured by using a laser Doppler blood-flowmeter (FLO-N1 produced by OMEGAWAVE, INC.), a microsphere (DYE-TRAK VII+ produced by Triton Technology Ltd.), or the like. Furthermore, changes in the amounts of the compositions which are delivered to various organs due to the increase in blood flow can be determined by the distribution of intravenously administered pigments such as Evans' Blue to said organs. Meanwhile, though Evans' Blue itself is not a medicament, it has been reported that the amounts of medicaments which are delivered can be estimated by the above method (Journal of Neurosurgery 2004; 101: 303-309). Namely, Evans' Blue is a pigment having a molecular weight of 960.08, and its use as a pharmaceutical model molecule for examining the delivery of medicaments has been established.

Blood pressure can be measured by inserting a catheter into the arteries, and measuring over time using a pressure sensor (Transducer TP-400T produced by Nihon Kohden Corporation), an amplifier (AP-601G produced by Nihon Kohden Corporation), and a recorder (MacLab/16S produced by ADInstruments).

EXAMPLES

The following non-limiting examples will further illustrate the present invention.

Test Example 1

Evaluating the variations in blood pressure and blood flow when administering arginine to rats (1) Outline of the Test:

(a) The changes in systemic blood pressure and the effect of increasing the blood flow in the capillaries of the skin of the lower thighs were examined on rats upon administration of arginine.

(b) The subjects were male SD rats having a body weight of around 400 g.

(c) Rats were anesthetized by pentobarbital and a catheter was inserted into their arteries. Then, blood pressure was measured and recorded over time. Furthermore, a probe(s) of a laser Doppler blood-flowmeter was fixed on the skin of the lower thighs, and the blood flow at the skin surface was measured and recorded over time. Arginine was adjusted to pH 7.4 with citric acid and continuously injected at a constant speed through the jugular vein at dosages of 50, 150, and 500 mg per 1 kg of body weight over 30 minutes. The blood pressure was observed before and after the treatment, as well as the blood flow of the skin on the lower thighs. Three rats were used per one administration and the evaluation was conducted by the variation of the average values of the three rats. A saline solution was administered to a control group.

(d) After the administration of arginine, the amount of blood which was flowing to the skin of the lower thighs increased in all rats to which 50 mg or more of arginine per 1 kg of the body weight was administered. As a result, it was confirmed that the blood flow was increased. The lowering of blood pressure beyond 11 mmHg was not observed in rats to which 150 mg or less of arginine per 1 kg of the body weight was administered. However, the lowering of blood pressure was observed in rats to which 500 mg or more of arginine per 1 kg of the body weight was administered. Two out of three rats died due to the rapid reduction of blood pressure.

(e) From the above results, while the reduction of blood pressure and the increase of blood flow were observed in the rats to which 500 mg of arginine per 1 kg of the body weight was administered, the increase of blood flow while slightly lowering blood pressure was observed in the rats to which 150 mg or less of arginine per 1 kg of the body weight was administered. Thus, it was thought that the administration of arginine in the amount defined in the present invention caused the increase of blood flow while slightly lowering blood pressure.

(2) Details of the Test (a) Constitution of each administration group: See Table 1.

TABLE 1

| Administration groups | Composition | Arginine concentration and amount of the admin'd solution |
|---|---|---|
| Control group | A saline solution | 0 mg/mL<br>5 mL/kg/30 mins. |

TABLE 1-continued

| Administration groups | Composition | Arginine concentration and amount of the admin'd solution |
|---|---|---|
| 50 mg of arginine per 1 kg of the body weight admin'd group | Arginine, Citric acid | 10 mg/mL 5 mL/kg/30 mins. |
| 150 mg of arginine per 1 kg of the body weight admin'd group | Arginine, Citric acid | 30 mg/mL 5 mL/kg/30 mins. |
| 500 mg of arginine per 1 kg of the body weight admin'd group | Arginine, Citric acid | 100 mg/mL 5 mL/kg/30 mins. |

(b) Measurement of blood pressure: The blood pressure in the catheter inserted into the arteries was measured and recorded over time by using a pressure sensor (Transducer TP-400T produced by Nihon Kohden Corporation), an amplifier (AP-601G produced by Nihon Kohden Corporation), and a recorder (MacLab/16S produced by ADInstruments).

(c) Measurement of blood flow: A thin probe(s) connected to a laser Doppler blood-flowmeter (FLO-N1 produced by OMEGAWAVE, INC.) was attached to the skin surface. Then, the amount of blood, the speed thereof, and the blood flow were measured by irradiating a laser.

(d) Test Results: Table 2 shows changes in the blood pressure and the blood flow which were observed in the arginine administration test. The blood pressure and the blood flow were measured right before injection of arginine, 20 to 30 minutes after the injection (for dosages of 50 mg or 150 mg), and 50 to 60 minutes after the injection (for the dosage of 500 mg). The results are expressed as averages of the measured values over 10 minutes.

TABLE 2

| Administration groups | Maximum variation of blood pressure | Maximum increasing rate of blood flow (Before administration: 100%) |
|---|---|---|
| Control group | −11 mmHg | +9.47% |
| 50 mg of arginine per 1 kg of the body weight admin'd group | −6 mmHg | +43.9% |
| 150 mg of arginine per 1 kg of the body weight admin'd group | −8 mmHg | +29.3% |
| 500 mg of arginine per 1 kg of the body weight admin'd group | −118 mmHg | +85.0% |

Test Example 2

Measurement of Blood Flow in the Capillaries of Various Organs with the Microsphere Method (1) Outline of the Test:

(a) The changes of blood flow in the capillaries of several organs were examined on rats while administering arginine.

(b) The subjects were male SD rats having a body weight of around 400 g.

(c) Rats were anesthetized by pentobarbital. Then, arginine was adjusted to pH 7.4 with citric acid and continuously injected at a constant speed through the jugular vein in dosages of 0, 50, or 150 mg per 1 kg of the body weight over 30 minutes. Before and after the administration of arginine, yellow and red microspheres were each injected using the catheter placed in the left ventricle via the jugular vein. Then, the blood flow for each organ before and after the administration of arginine was compared by comparing the amounts of the microspheres which were distributed from the heart to the capillaries of the organs of the entire body.

(d) In all of the organs measured, that is, muscles, digestive tract, liver, kidneys, spleen, heart, brain, adipose tissues, and abdominal skin, the tendency was observed that the increase in blood flow in the capillaries was dose-dependent on arginine. In the rats to which 150 mg of arginine per 1 kg of the body weight was administered, the blood flow in the capillaries increased for all organs measured. On the other hand, even in the rats to which 50 mg of arginine per 1 kg of the body weight was administered, it was confirmed that the blood flow in the capillaries of the muscles and the brain was significantly increased.

(e) From the above results, the increase of blood flow in the capillaries of a wide range of organs is shown in the rats to which 150 mg of arginine per 1 kg of the body weight was administered. On the other hand, the increase of blood flow in the capillaries of the muscles and the brain was clearly shown in the rats to which 50 mg of arginine per 1 kg of the body weight was administered. Thus, it was thought that the administration of arginine in the dosage of the present invention was particularly notable in the muscles and the brain.

(f) The variation of blood pressure was within 10 mmHg. Therefore, it was shown that blood pressure did not change when administering 50 or 150 mg of arginine per 1 kg of the body weight.

(2) Details of the Test (a) Constitution of each administration group: See Table 3.

TABLE 3

| Administration groups | Composition | Arginine concentration and amount of the admin'd solution |
|---|---|---|
| Control group | A saline solution | 0 mg/mL 5 mL/kg/30 mins. |
| 50 mg of arginine per 1 kg of the body weight admin'd group | Arginine, Citric acid | 10 mg/mL 5 mL/kg/30 mins. |
| 150 mg of arginine per 1 kg of the body weight admin'd group | Arginine, Citric acid | 30 mg/mL 5 mL/kg/30 mins. |

(b) Operation: Catheters were inserted into the carotid artery, jugular vein, and femoral artery of rats under anesthesia. Then, the microsphere and arginine were administered respectively, and the sample blood was collected from each catheter.

(c) Measurement of blood flow: Right before and just after the 30-minute administration of arginine, yellow and red microspheres were injected using the catheter placed in the left ventricle. After taking enough time from the second administration of the microsphere, the rats were euthanasized, and the muscles, digestive tracts, liver, kidneys, spleen, heart, brain, adipose tissues, and abdominal skin were extracted. Then, the microspheres contained in each organ were collected and the rate of change in blood flow was calculated for each organ from the amount of the microspheres.

(d) Test Results: Table 4 shows changes in blood flow which were observed in the arginine administration test.

TABLE 4

Changes in blood flow after the administration of arginine
(Variation before the administration is 100%)

|  | 0 mg/kg of body weight | 50 mg/kg of body weight | 150 mg/kg of body weight |
|---|---|---|---|
| Muscles | 102% | 164% | 157% |
| Abdominal skin | 95% | 117% | 134% |
| Back skin | 95% | 107% | 118% |
| Adipose tissues | 87% | 99% | 116% |
| Kidneys | 68% | 86% | 91% |
| Spleen | 96% | 104% | 115% |
| Duodenum | 109% | 123% | 142% |
| Liver | 65% | 92% | 101% |
| Heart | 121% | 126% | 140% |
| Brain | 115% | 126% | 137% |

Test Example 3

Measurement of the Concentration of Free Arginine in the Blood Plasma when Intravenously Administering Arginine (1) Outline of the Test:

(a) The concentration of free arginine in the blood plasma was examined in rats when arginine is intravenously administered.

(b) The subjects were male SD rats having a body weight of around 400 g.

(c) Rats were anesthetized by pentobarbital. Then, arginine was adjusted to pH 7.4 with citric acid and continuously injected at a constant speed through the jugular vein in dosages of 0, 50, or 150 mg per 1 kg of the body weight over 30 minutes starting from 10:00 a.m. Right before such administration of arginine and every minutes from 10 to 40 minutes after the end of the administration, blood was collected from the catheter placed in the femoral artery. Then, the concentration of free arginine in the blood plasma was measured.

(d) In the rats to which 50 mg of arginine per 1 kg of the body weight was administered, the concentration of free arginine in the blood plasma rose by 46.1 micrograms per 1 mL at maximum. In the rats to which 150 mg of arginine per 1 kg of the body weight was administered, the concentration of free arginine in the blood plasma rose by 177.5 micrograms per 1 mL at maximum. On the other hand, in the control group to which arginine was not administered, the concentration of free arginine in the blood plasma did not rise.

(e) From the above results, when administering 50 or 150 mg of arginine per 1 kg of the body weight, for which the increase of blood flow was observed, it was confirmed that each of the concentrations of free arginine in the blood plasma rose by 15.7 to 46.1 micrograms per 1 mL or 77.2 to 177.5 micrograms per 1 mL.

(f) As for blood pressure, Test Example 1, wherein the same amounts of arginine were administered, shows that the blood pressure did not change. Therefore, it was confirmed that blood pressure was not changed by the variation of the concentrations of arginine in the blood plasma within the above range.

(2) Details of the Test
(a) Compositions of each administered solutions: See Table 5.

TABLE 5

| Administration groups | Composition | Arginine concentration and amount of the admin'd solution |
|---|---|---|
| Control group | A saline solution | 0 mg/mL<br>5 mL/kg/30 mins. |
| 50 mg of arginine per 1 kg of the body weight admin'd group | Arginine, Citric acid | 10 mg/mL<br>5 mL/kg/30 mins. |
| 150 mg of arginine per 1 kg of the body weight admin'd group | Arginine, Citric acid | 30 mg/mL<br>5 mL/kg/30 mins. |

(b) Administration: An aqueous solution of dissolved arginine was continuously injected at a constant speed through the catheter placed in the jugular vein in the dosages of 50 or 150 mg per 1 kg of the body weight over 30 minutes.

(c) Measurement of the concentration of free arginine in the blood plasma: Before and after the administration of arginine, the rats' blood was collected from the catheter placed in their femoral arteries. Then, the concentration of free arginine contained in the blood was measured with an amino acid analyzer (L8500, the amino acid analyzer produced by Hitachi, Ltd.)

(d) Test results: Table 6 shows changes over time of the increase in the concentration of free arginine in the blood plasma.

TABLE 6

Average values of increase in the concentration of free arginine in the blood plasma (unit: µg/mL)

| Administration groups | 10 minutes later | 20 minutes later | 30 minutes later | 40 minutes later |
|---|---|---|---|---|
| Control group | 0.2 | 0.5 | 0.4 | 0.6 |
| 50 mg of arginine per 1 kg of the body weight admin'd group | 43.6 | 46.1 | 38.8 | 15.7 |
| 150 mg of arginine per 1 kg of the body weight admin'd group | 155.5 | 114.8 | 177.5 | 77.2 |

As seen in the administration of 50 or 150 mg of arginine per 1 kg of the body weight, by which the increase of blood flow was observed, the range of rise of the concentration of free arginine in the blood plasma was about 15 to 180 micrograms per 1 mL of blood plasma. Thus, it was shown that the rise of the concentration of free arginine in the blood plasma which was necessary for increasing blood flow was within the above range.

Test Example 4

Evaluating the Variations in Blood Pressure and Blood Flow when Administering Arginine and Glutamine to Rats (1) Outline of the Test:
(a) The changes of the systemic blood pressure and the effect of increasing the blood flow in the capillaries of the skin of lower thighs were examined in rats which had been administered arginine and glutamine.

(b) The subjects were male SD rats having a body weight of around 400 g.

(c) Rats were anesthetized by pentobarbital and a catheter was inserted to their arteries. Then, blood pressure was measured and recorded over time. Furthermore, a probe(s) of a laser Doppler blood-flowmeter was fixed on the skin of the lower thighs, and the blood flow at the skin surface was measured and recorded over time. Arginine neutralized with citric acid or equal quantities of arginine and glutamine was administered by continuously injecting at a constant speed at the dosage of 50 mg of arginine per 1 kg of the body weight over 30 minutes. The blood pressure and the blood flow of the skin of the lower thighs before and after the treatment were observed. Three rats were used per one administration, and evaluation was conducted by the variation of the average value of the three rats. A saline solution was administered to a control group.

(d) It was confirmed that, after the administration of arginine, the amount of blood flow of the skin on the lower thighs increased by a maximum of +20.0% in all rats to which 50 mg of arginine per 1 kg of the body weight was administered. Meanwhile, it was confirmed that the amount of blood flow of the skin on the lower thighs increased by at maximum of +39.9% in the rats to which the solution mixed with 50 mg of arginine per 1 kg of the body weight and an equal quantity of glutamine was administered.

(e) From the above results, since the administration of the solution mixed with 50 mg of arginine per 1 kg of the body weight and an equal quantity of glutamine particularly increased blood flow as compared with that of 50 mg of arginine only per 1 kg of the body weight, it was thought that the concurrent use of glutamine enhanced the increase of blood flow by the administration of arginine in the present invention.

(2) Details of the Test (a) Constitution of each administration group: See Table 7.

TABLE 7

| Administration groups | Composition | Arginine concentration and amount of the admin'd solution |
|---|---|---|
| Control group | A saline solution | 0 mg/mL<br>5 mL/kg/30 mins. |
| 50 mg of arginine per 1 kg of the body weight admin'd group | Arginine,<br>Citric acid | 10 mg/mL<br>5 mL/kg/30 mins. |
| 50 mg of arginine per 1 kg of the body weight + 50 mg of glutamine per 1 kg of the body weight admin'd group | Arginine,<br>Glutamine<br>Citric acid | 10 mg/mL<br>5 mL/kg/30 mins. |

(b) Measurement of blood pressure: The blood pressure in the catheter inserted into the arteries was measured and recorded over time by using a pressure sensor (Transducer TP-400T produced by Nihon Kohden Corporation), an amplifier (AP-601G produced by Nihon Kohden Corporation), and a recorder (MacLab/16S produced by ADInstruments).

(c) Measurement of blood flow: A thin probe(s) connected to a laser Doppler blood-flowmeter (FLO-N1 produced by OMEGAWAVE, INC.) was attached to the skin surface. Then, the amount of blood, the speed thereof and the blood flow were measured by irradiating a laser.

(d) Test Results: Table 8 shows changes over time in blood pressure and blood flow which were observed in the arginine administration test. The blood pressure and the blood flow were measured before injection of arginine and 20 to 30 minutes after the injection, and are expressed as averages of values measured over 10 minutes.

TABLE 8

| Administration groups | Maximum variation of blood pressure | Maximum increasing rate of blood flow (Before administration: 100%) |
|---|---|---|
| Control group | −5.38 mmHg | +9.47% |
| 50 mg of arginine per 1 kg of the body weight admin'd group | +11.4 mmHg | +20.0% |
| 50 mg of arginine per 1 kg of the body weight + 50 mg of glutamine per 1 kg of the body weight admin'd group | +22.1 mmHg | +39.9% |

Test Example 5

Measurement of Amounts of the Compositions Which Were Delivered to Various Organs by using Evans' Blue (1) Outline of the Test:

(a) Evans' Blue (Wako Pure Chemical Industries, Ltd.) was used as a model to estimate the amount of a delivered composition, such as a pharmaceutical composition. The changes in the amount of Evans' Blue which was delivered was measured in several organs to which arginine had been administered.

(b) The subjects were male SD rats having a body weight of around 400 g.

(c) Rats were anesthetized by pentobarbital. Then, arginine was adjusted to pH 7.4 with citric acid and continuously injected at a constant speed into the jugular vein in dosages of 0, 50 or 150 mg per 1 kg of the body weight over 30 minutes. Before and after such administration of arginine, Evans' Blue was injected using the catheter which had been placed in the jugular vein. Then, the delivered amounts of the arginine compositions to each organ were compared by comparing the amounts of Evans' Blue which had been distributed to the organs of the entire body using a spectrophotometer.

(d) In muscles, digestive tract, liver, kidneys, spleen, brain, adipose tissues, and skin measured this time, the tendency was observed that the delivered amounts of Evans' Blue to the organs increased when using the dosage of 50 or 150 mg of arginine per 1 kg of the body weight.

(e) From the above results, in the rats to which 50 mg of arginine per 1 kg of the body weight was administered, the delivered amount of Evans' Blue increased. Thus, it was shown that the delivered amounts of the compositions to organs were increased by the administration of arginine in the dosage of the present invention.

(2) Details of the Test (a) Constitution of each administration group: See the following Table 9.

TABLE 9

| Administration groups | Composition | Arginine concentration and amount of the admin'd solution |
|---|---|---|
| Control group | A saline solution | 0 mg/mL<br>5 mL/kg/30 mins. |
| 50 mg of arginine per 1 kg of the body weight admin'd group | Arginine,<br>Citric acid | 10 mg/mL<br>5 mL/kg/30 mins. |

TABLE 9-continued

| Administration groups | Composition | Arginine concentration and amount of the admin'd solution |
|---|---|---|
| 150 mg of arginine per 1 kg of the body weight admin'd group | Arginine, Citric acid | 30 mg/mL 5 mL/kg/30 mins. |

(b) Operation: A catheter was inserted into the jugular vein of rats under anesthesia. Then, a blood sample was collected from the catheter.

(c) Measurement of the delivered amounts of Evans' Blue: An aqueous solution of Evans' Blue (50 mg/mL) was injected using the catheter placed in the jugular vein just after the 30 minute administration of arginine. After sufficient time, the rats were euthanasized, and the muscles, digestive tracts, liver, kidneys, spleen, heart, brain, adipose tissues, and abdominal skin were extracted. Then, Evans' Blue was released by immersing each organ in a formalin solution, and the amount of Evans' Blue in each organ was calculated from the absorbance obtained by the spectrophotometer.

(d) Test results: Table 10 shows the changes in the amount of Evans' Blue which were observed in the arginine administration test.

TABLE 10

Changes in the amounts of Evans' Blue after administering arginine (Variation before the administration is 100%)

|  | 50 mg/kg of BW | 150 mg/kg of BW |
|---|---|---|
| Gastrocnemius muscle | 219% | 154% |
| Soleus muscle | 123% | 125% |
| Abdominal skin | 124% | 207% |
| Back skin | 315% | 331% |
| Adipose tissues | 430% | 160% |
| Kidneys | 161% | 128% |
| Spleen | 101% | 92% |
| Duodenum | 143% | 85% |
| Liver | 181% | 173% |
| Heart | 87% | 85% |
| Brain | 169% | 128% |

While the invention has been described in detail with reference to exemplary embodiments thereof, it will be apparent to one skilled in the art that various changes can be made, and equivalents employed, without departing from the scope of the invention. Each of the aforementioned documents is incorporated by reference herein in its entirety.

We claim:

1. A method for increasing blood flow without lowering systemic blood pressure consisting essentially of administering 25 mg/kg body weight to 150 mg/kg body weight arginine in combination with 25 mg/kg body weight to 300 mg/kg body weight L-glutamine per dose to a patient in need of increased blood flow without lowering systemic blood pressure.

2. The method according to claim 1, wherein said blood flow is increased in capillaries.

3. The method according to claim 1, wherein said blood flow is increased in muscles, heart or adipose tissue.

* * * * *